US012697499B2

(12) United States Patent　(10) Patent No.: US 12,697,499 B2
Kuno et al.　(45) Date of Patent: Aug. 4, 2026

(54) AUTOMATED EXTERNAL DEFIBRILLATOR

(71) Applicant: NIHON KOHDEN CORPORATION, Tokyo (JP)

(72) Inventors: Ryosuke Kuno, Tokorozawa (JP); Junichi Miyachi, Tokorozawa (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 181 days.

(21) Appl. No.: 18/729,387

(22) PCT Filed: Oct. 26, 2022

(86) PCT No.: PCT/JP2022/040016
§ 371 (c)(1),
(2) Date: Jul. 16, 2024

(87) PCT Pub. No.: WO2023/135895
PCT Pub. Date: Jul. 20, 2023

(65) Prior Publication Data
US 2025/0082946 A1　Mar. 13, 2025

(30) Foreign Application Priority Data
Jan. 17, 2022　(JP) ................................. 2022-005110

(51) Int. Cl.
*A61N 1/39* (2006.01)
(52) U.S. Cl.
CPC ......... *A61N 1/3904* (2017.08); *A61N 1/3975* (2013.01); *A61N 1/3993* (2013.01)
(58) Field of Classification Search
CPC .................................................. A61B 5/361
See application file for complete search history.

(56) References Cited

U.S. PATENT DOCUMENTS 5,474,574 A　12/1995　Payne et al.
6,088,616 A　7/2000　Olson et al.
(Continued)

FOREIGN PATENT DOCUMENTS

EP　3 777 970 A1　2/2021
EP　3 903 879 A1　11/2021
(Continued)

OTHER PUBLICATIONS

"Dumitru, et al., Chapter 3—Instrumentation, 2002, Electrodiagnostic Medicine, Version 2, https://www.sciencedirect.com/topics/nursing-and-health-professions/skin-electrode" (Year: 2002).*
(Continued)

*Primary Examiner* — Michael T. Holtzclaw
(74) *Attorney, Agent, or Firm* — Sughrue Mion, PLLC

(57) ABSTRACT

An automated external defibrillator is configured to automatically execute a defibrillation process of delivering an electric shock for defibrillation to a heart of a subject. The defibrillator includes: a processor; and a memory that stores a computer-readable instruction that when executed by the processor, causes the defibrillator to perform operations including: receiving a physiological signal of the subject through an electrode pad; determining whether the defibrillation process is necessary based on the physiological signal; and determining whether the electrode pad is attached to the subject and a predetermined operation has been performed on the defibrillator. When the defibrillation process is necessary, the defibrillator cancels the defibrillation process while maintaining an on-state of a power supply thereof, in response to a result of the determination as to whether the electrode pad is attached to the subject and the predetermined operation has been performed on the defibrillator.

9 Claims, 4 Drawing Sheets

(56)          References Cited

U.S. PATENT DOCUMENTS

| | | |
|---|---|---|
| 2007/0162075 A1 | 7/2007 | O'Hara |
| 2012/0046706 A1 | 2/2012 | Anderson et al. |
| 2014/0100497 A1* | 4/2014 | Hayashi ............... A61N 1/3611<br>601/41 |
| 2015/0005836 A1 | 1/2015 | Jonsen et al. |
| 2016/0235997 A1 | 8/2016 | Anderson et al. |
| 2017/0304640 A1 | 10/2017 | Sato |
| 2018/0236251 A1 | 8/2018 | Anderson et al. |
| 2019/0076666 A1* | 3/2019 | Medema .............. A61N 1/3987 |

FOREIGN PATENT DOCUMENTS

| | | | | |
|---|---|---|---|---|
| JP | 2007-522859 A | 8/2007 | | |
| JP | 2012-525179 A | 10/2012 | | |
| JP | 2015-509024 A | 3/2015 | | |
| JP | 2016-146932 A | 8/2016 | | |
| WO | WO-2004054656 A1 * | 7/2004 | ........... | A61B 5/7203 |
| WO | 2006/016289 A2 | 2/2006 | | |

OTHER PUBLICATIONS

Communication dated Jul. 29, 2025, issued by the Japanese Patent Office in Japanese Application No. 2022-005110.

International Search Report (PCT/ISA/210) issued Feb. 2, 2023 by the International Searching Authority in International Patent Application No. PCT/JP2022/040016.

Written Opinion (PCT/ISA/237) issued Feb. 2, 2023 by the International Searching Authority in International Patent Application No. PCT/JP2022/040016.

* cited by examiner

AUTOMATED EXTERNAL DEFIBRILLATOR

CROSS-REFERENCE TO RELATED APPLICATIONS

This application is a National Phase Entry of PCT International Application No. PCT/JP2022/040016 filed on Oct. 26, 2022, which claims priority to Japanese Patent Application No. 2022-005110 filed on Jan. 17, 2022, the entire contents of which are incorporated herein by reference.

TECHNICAL FIELD

The present disclosure relates to an automated external defibrillator.

BACKGROUND ART

Currently, automated external defibrillators (hereinafter referred to as "AEDs") have been rapidly widespread. Such an AED delivers a strong electric shock for defibrillation to the heart of a patient who has suffered a sudden cardiac arrest due to ventricular fibrillation, so as to restore a cardiac function of the patient. For example, U.S. Pat. No. 5,474,574 discloses a fully automatic AED that automatically executes a defibrillation process of delivering an electric shock for defibrillation to the heart of a patient without requiring any input operation made on the AED by an operator.

By the way, in a case where the patient regains consciousness before execution of the defibrillation process of delivering an electric shock to the patient, there can be anticipated a situation in which the operator wants to keep on measuring the condition of the patient by the AED while canceling the defibrillation process (or even in a case where the measurement of the condition of the patient is suspended, the operator wants to keep the AED at a state in which the AED can resume the measurement immediately). In this respect, according to the fully automatic AED disclosed in U.S. Pat. No. 5,474,574, a power supply of the fully automatic AED must be turned off completely in order to cancel the defibrillation process. Therefore, in order to analyze the condition of the patient again by the AED after the defibrillation process is canceled, the operator must wait for the AED to start an ECG analysis process after reactivating the AED. However, it may be anticipated that a cardiac function of the patient may suddenly change during the waiting time. Therefore, it is desirable that the defibrillation process can be canceled while an on state of the power supply of the AED is maintained. Thus, there is room for further improving usability of the AED in a scene where the operator wants to cancel the defibrillation process.

SUMMARY

The present disclosure aims to improve usability of an AED. In particular, the present disclosure aims to improve the usability of the AED in a scene in which an operator wants to cancel a defibrillation process.

According to one or more aspects of the present disclosure, there is provided an automated external defibrillator that is configured to automatically execute a defibrillation process of delivering an electric shock for defibrillation to a heart of a subject. The automated external defibrillator includes: a processor; and a memory that stores a computer-readable instruction that when executed by the processor, causes the automated external defibrillator to perform operations including: receiving a physiological signal of the subject through an electrode pad; determining whether the defibrillation process is necessary or not based on the physiological signal; and determining whether the electrode pad is attached to the subject and a predetermined operation has been performed on the automated external defibrillator or not. When the defibrillation process is necessary, the automated external defibrillator cancels the defibrillation process while maintaining an on-state of a power supply of the automated external defibrillator, in response to a result of the determination as to whether the electrode pad is attached to the subject and the predetermined operation has been performed on the automated external defibrillator or not.

According to the aforementioned configuration, it is determined whether the electrode pad is attached to the subject and the predetermined operation has been performed on the automated external defibrillator (hereinafter referred to as "AED") or not. According to the result of the determination, the defibrillation process of delivering an electric shock to the subject is canceled while the on state of the power supply of the AED is maintained. Thus, unlike the background-art fully automatic AED, the defibrillation process can be canceled while the on state of the power supply of the AED is maintained. In this respect, according to the background-art fully automatic AED, the power supply of the AED must be turned off completely in order to cancel the defibrillation process. Therefore, to analyze an electrocardiogram (hereinafter referred to as ECG) of the subject again, there is a waiting time until the AED moves to the ECG analysis process (or a process of determining whether the defibrillation process is necessary or not) after the AED is reactivated. On the other hand, according to the present configuration, only the defibrillation process of the AED can be canceled while the on state of the power supply of the AED is maintained. Therefore, usability of the AED can be improved spectacularly.

DESCRIPTION OF EMBODIMENT

An embodiment will be described below with reference the drawings. For convenience of explanation, dimensions of each member shown in each of the drawings may be different from actual dimensions of the member.

Figure 1:
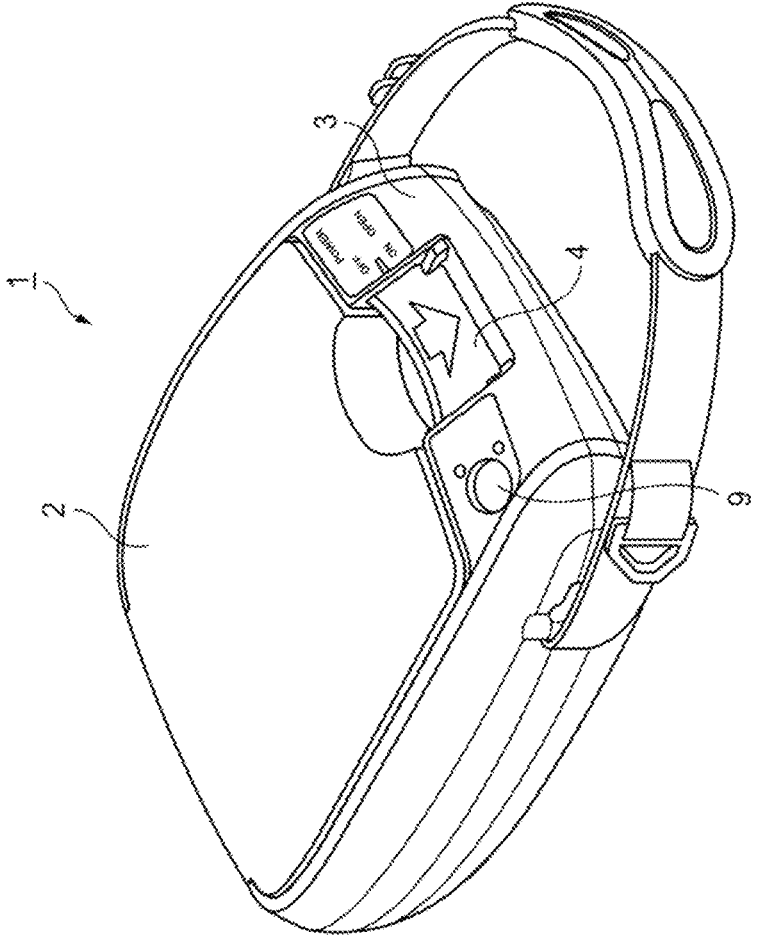
FIG. 1 is a perspective view illustrating an automated external defibrillator (hereinafter referred to as "AED") whose cover has been closed.
Figure 2:
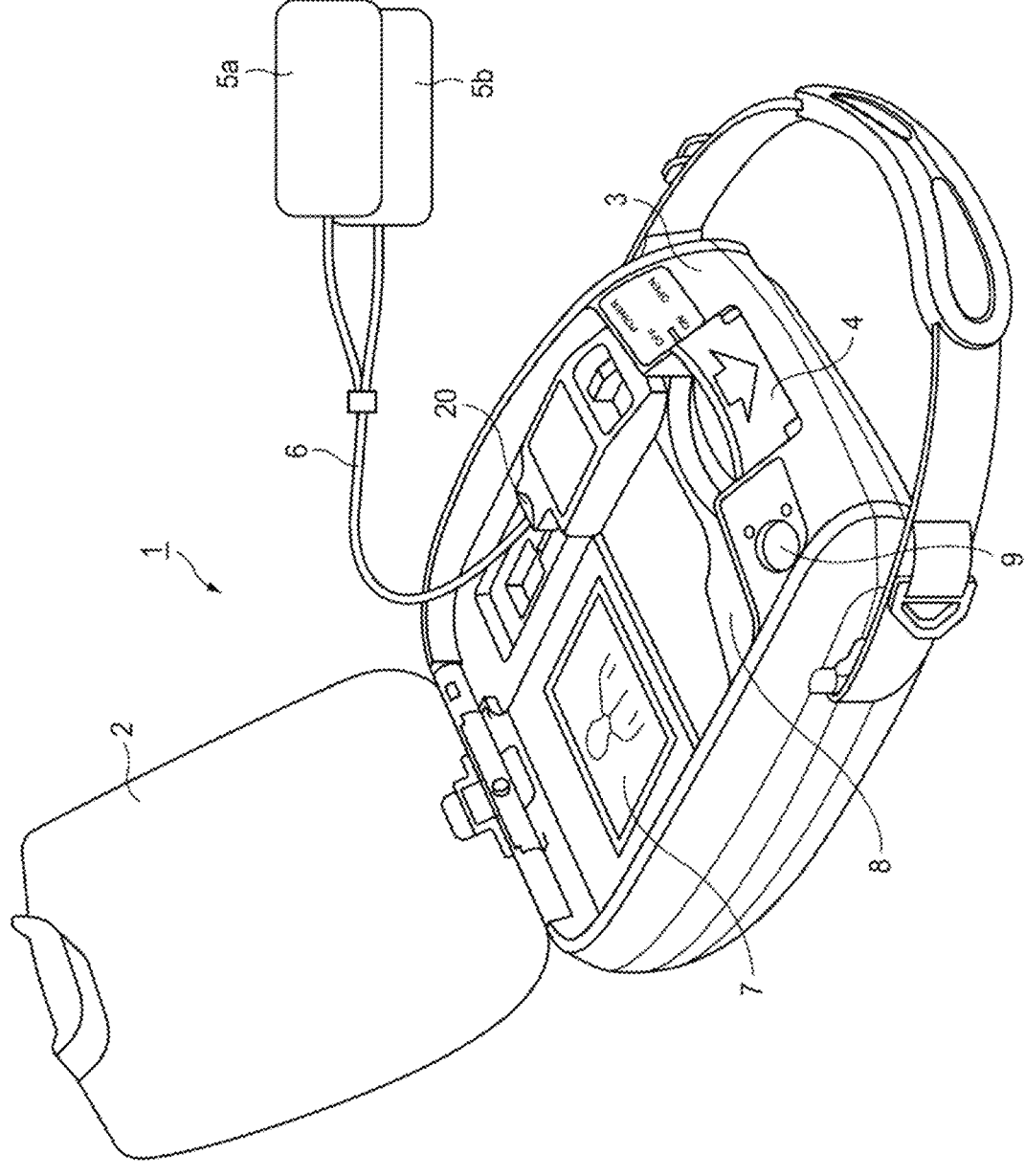
FIG. 2 is a perspective view illustrating the AED whose cover has been opened.
Figure 3:
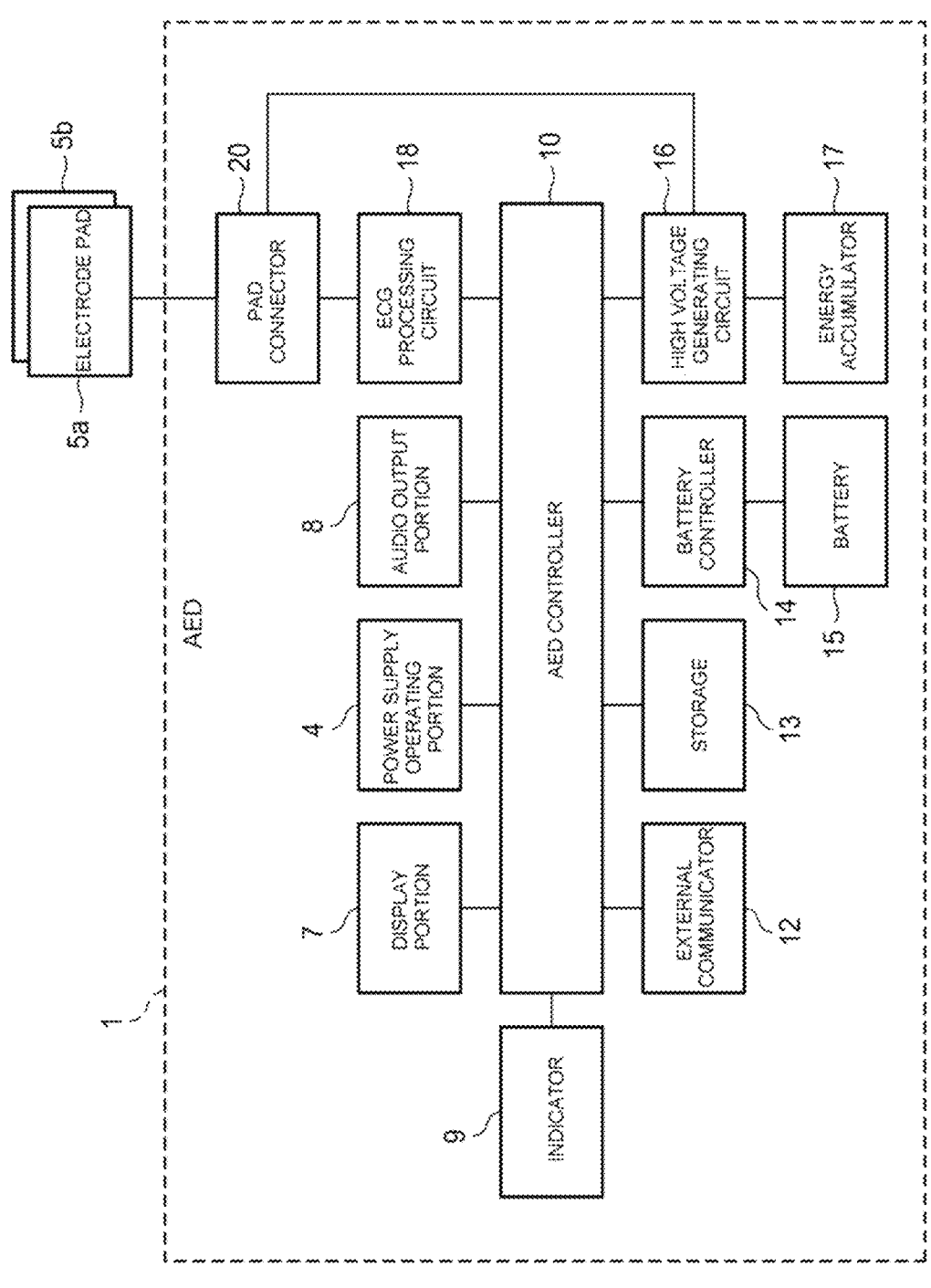
FIG. 3 is a block diagram illustrating the configuration of the AED.

First, the configuration of an automated external defibrillator 1 (hereinafter referred to as AED 1) will be described below with reference to FIGS. 1 through 3. FIG. 1 is a perspective view illustrating the AED 1 whose cover 2 has been closed. FIG. 2 is a perspective view illustrating the AED 1 whose cover 2 has been opened. FIG. 3 is a block diagram illustrating the configuration of the AED 1. The AED 1 according to the present embodiment is a fully automatic AED. That is, the AED 1 is configured to automatically execute a defibrillation process of delivering an electric shock for defibrillation to the heart of a patient (hereinafter also referred to as "subject") without requiring any input operation made by an operator. Therefore, an electric shock button or the like for starting the defibrillation process (electric shock) is not provided in the AED 1, as shown in FIG. 2.

As shown in FIG. 1, the AED 1 has a housing 3, the cover 2 connected to the housing 3, and a power supply operating portion 4. When the power supply operating portion 4 is pressed toward a direction indicated by an arrow shown in FIG. 1, an operation for turning on a power supply of the AED 1 is performed on the power supply operating portion 4, and the cover 2 is opened, as shown in FIG. 2. In a state in which the cover 2 is closed, the power supply of the AED 1 is turned off. On the other hand, in a state in which the cover 2 is opened, the power supply of the AED 1 is turned on. When the cover 2 is closed, the AED 1 changes from the state shown in FIG. 2 to the state shown in FIG. 1, and an operation of turning off the power supply of the AED 1 is performed on the power supply operating portion 4. Thus, according to the AED 1 according to the present embodiment, when the cover 2 is opened, the operation of turning on the power supply of the AED 1 (hereinafter referred to as "power-on operation") is performed on the power supply operating portion 4. On the other hand, when the cover 2 is closed, the operation of turning off the power supply of the AED 1 (hereafter referred to as "power-off operation") is performed on the power supply operating portion 4. For example, see Japanese Patent No. 5046031 for details of the power-on operation or the power-off operation made in response to the opening or closing of the cover 2.

Next, the configuration of the AED 1 will be described below with reference to FIG. 2 and FIG. 3. As shown in FIG. 2 and FIG. 3, the AED 1 is provided with an AED controller 10, a high voltage generating circuit 16, an energy accumulator 17, a battery 15, a battery controller 14, a storage 13, and an external communicator 12. In addition, the AED 1 is further provided with an ECG processing circuit 18, a pad connector 20, an audio output portion 8, the power supply operating portion 4, a display portion 7, and an indicator 9.

The AED 1 is a medical device configured to automatically execute the defibrillation process so as to restore a cardiac function of the patient who has suffered a cardiac arrest due to ventricular fibrillation. Moreover, the AED 1 is configured to measure an electrocardiogram (hereinafter referred to as ECG) of the patient. The AED controller 10 is configured to control the respective constituent components provided in the AED 1. The AED controller 10 is, for example, constituted by a microcontroller including a processor and a memory, and an analog electronic circuit including at least an AD convertor (analog-to-digital conversion circuit). The processor includes at least one of, for example, a CPU (Central Processing Unit), an MPU (Micro Processing Unit), and a GPU (Graphics Processing Unit). The memory includes an ROM (Read Only Memory) and an RAM (Random Access Memory). The processor may be configured to expand, onto the RAM, a program (computer-readable instruction) designated from various programs incorporated in the storage 13 or the ROM and to execute various processes (e.g. a series of processes shown in FIG. 4) in cooperation with the RAM.

The high voltage generating circuit 16 is constituted by an electric charge control circuit and an electric discharge control circuit. The electric charge control circuit is configured to charge the energy accumulator 17 with electric energy for delivering an electric shock for defibrillation to the patient (subject). The electric discharge control circuit is configured to discharge the electric energy accumulated in the energy accumulator 17. The energy accumulator 17 is configured to accumulate the electrical energy for delivering an electric shock for defibrillation to the patient, and may be, for example, a high voltage film capacitor constituted by a plurality of dielectric films. The electrical energy discharged from the energy accumulator 17 is outputted from a pair of electrode pads 5a and 5b via the high voltage generating circuit 16 and the pad connector 20.

The battery 15 has a battery main body and a battery memory. The battery main body functions as the power supply configured to feed electric power to the respective constituent components of the AED 1. For example, the battery main body is a lithium primary battery. Information relevant to the battery, such as a remaining capacity of the battery is stored in the battery memory. The battery 15 may be replaceable. In the present example, the battery 15 is defined as a constituent component of the AED 1. However, the battery 15 may be defined as a separate constituent component (accessory) from the AED 1.

The battery controller 14 is provided with a circuit (such as a switching regulator or a series regulator) configured to convert the voltage of the battery 15 into a voltage required for the respective constituent components of the AED 1. Moreover, the battery controller 14 is configured to transmit a signal indicating the voltage of the battery 15 to the AED controller 10. The AED controller 10 may first determine usage of the battery 15 based on the signal transmitted from the battery controller 14, and then integrate the usage of the battery 15 to thereby determine the remaining capacity of the battery 15.

The storage 13 is configured to store the various programs for controlling the AED 1, image data displayed on the display portion 7, audio data outputted from the audio output portion 8, ECG data of the patient, data relevant to a usage state of the AED 1 (such as the remaining capacity of the battery and presence/absence of abnormality of the AED 1), etc. The storage 13 is, for example, constituted by a flash memory or a hard disk. The external communicator 12 is configured to transmit various data stored in the storage 13 to an external apparatus such as a management server. The external communicator 12 may be a wireless communication module supporting short-range wireless communication standards such as Bluetooth (registered trademark) and Wi-Fi (registered trademark). When the external communicator 12 is the wireless communication module, the external communicator 12 may have a transmitting and receiving antenna, a high frequency circuit, and a signal processing circuit. The external communicator 12 may, for example, transmit data relevant to the AED 1 to the management server on a communication network through a not-shown repeater. In this case, the AED 1 may be connected to the repeater by the short-range wireless communication.

The ECG processing circuit 18 is configured to process ECG signals outputted from the pair of electrode pads 5a and 5b attached to the patient. For example, the ECG processing circuit 18 may have a differential amplifier that amplifies a difference between an ECG signal outputted from one of the pair of electrode pads 5a and 5b and an ECG signal outputted from the other electrode pad, and an AD converter that converts the amplified difference between the ECG signals from an analog signal into a digital signal.

As shown in FIG. 2, the pair of electrode pads 5a and 5b are connected to the pad connector 20 through a pad cable 6. The pair of electrode pads 5a and 5b are removably attached to the AED 1, and may be disposable. Prior to use of the AED 1, the pair of electrode pads 5a and 5b may be received in a not-shown package. When the AED 1 is in use, the pair of electrode pads 5a and 5b are attached to the surface of the body of the patient. While the ECG signals of the patient are inputted to the pair of electrode pads 5a and 5b, electrical energy for delivering an electric shock to the heart of the patient is outputted from the pair of electrode pads 5a and 5b. In the present example, the electrode pads 5a and 5b are defined as accessories rather than constituent components of the AED 1, but may be defined as the constituent components of the AED 1.

The audio output portion 8 (an example of an output portion) is a speaker configured to audibly output voice guidance and a warning sound relevant to an operation of the AED 1 or treatment on the patient. The power supply operating portion 4 is configured to accept an operation for turning on or off the power supply of the AED 1 from an operator. In the present example, the power supply operating portion 4 accepts the power-on operation or the power-off operation in response to the opening or closing operation of the cover 2.

The display portion 7 (another example of the output portion) is configured to display, on a display screen, guidance relevant to the operation of the AED 1 or the treatment on the patient. The display portion 7 is, for example, constituted by a liquid crystal display, an organic EL display, or the like. The indicator 9 is configured to display the status of the AED 1. For example, the indicator 9 lights up in a first display color when the AED 1 is ready for use. On the other hand, the indicator 9 may light up in a second display color different from the first control when the AED 1 is not ready for use. In addition, an indicator indicating the remaining capacity of the battery may be provided in the AED 1.

Figure 4:
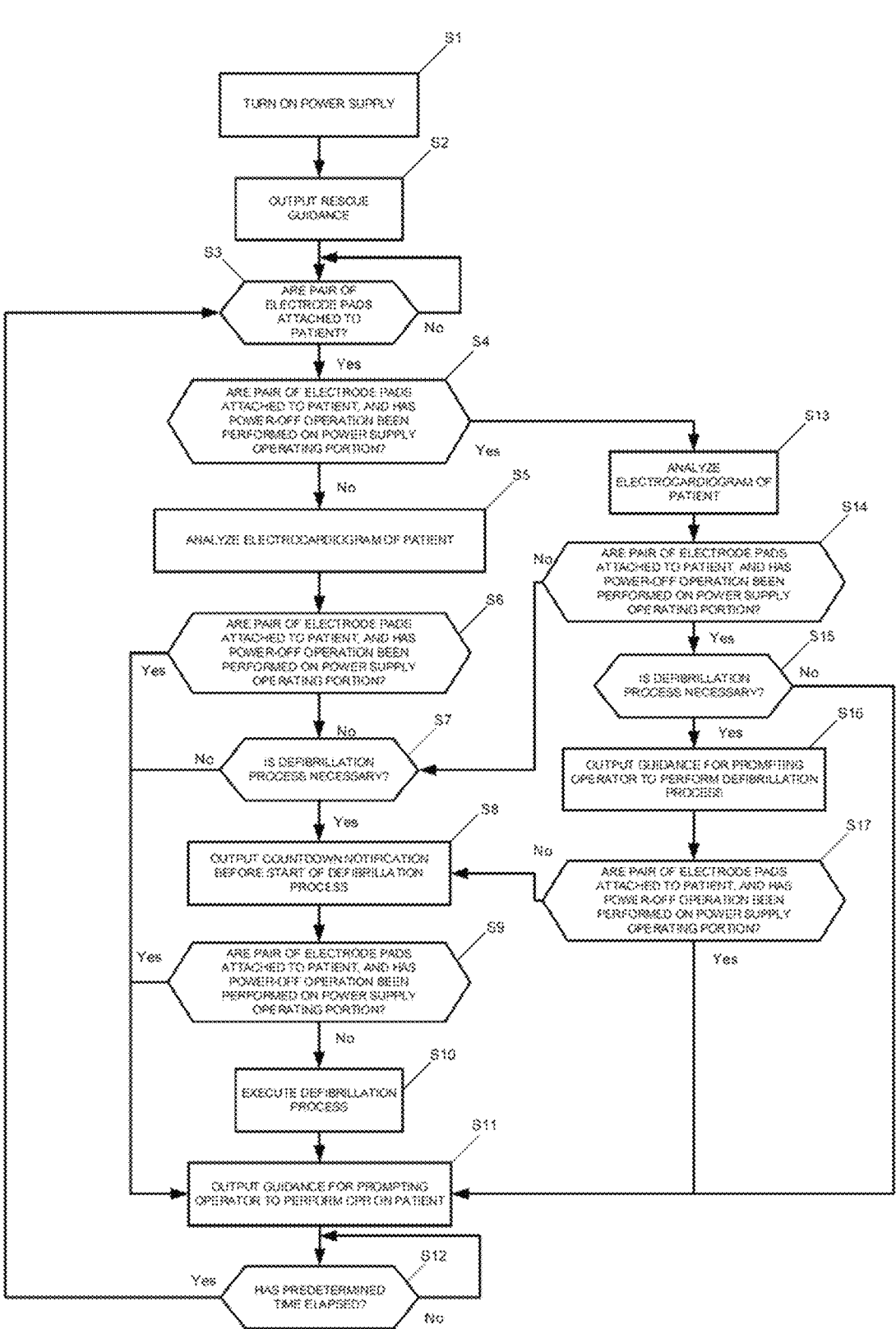
FIG. 4 is a flow chart for describing a series of processes executed by the AED.

Next, the series of processes executed by the AED 1 after the power supply is turned on will be described below with reference to FIG. 4. FIG. 4 is a flow chart for describing the series of processes executed by the AED 1 after the power supply is turned on. As shown in FIG. 4, in response to the cover 2 of the AED 1 opened by the operator, the power supply operating portion 4 accepts a power-on operation. The AED controller 10 turns on the power supply of the AED 1 based on a signal indicating the power-on operation (step S1). When the power supply is on, the AED controller 10 executes various initialization processes including internal operation checks. Next, the AED controller 10 audibly and/or visually outputs rescue guidance for rescuing a patient having a cardiac arrest (step S2). In this respect, the rescue guidance may be outputted audibly from the audio output portion 8 or may be displayed on the display screen of the display portion 7. In the present example, when information such as the guidance is outputted visually, it means that the information is displayed on the display portion 7. On the other hand, when the information is outputted audibly, it means that the information is outputted from the audio output portion 8.

Next, in a step S3, the AED controller 10 determines whether the pair of electrode pads 5a and 5b are attached to the surface of the body of the patient or not, based on an impedance value between the pair of electrode pads 5a and 5b. When, for example, the impedance value between the pair of electrode pads 5a and 5b is not larger than a predetermined value, the AED controller 10 may determine that the pair of electrode pads 5a and 5b are attached to the surface of the body of the patient. On the contrary thereto, when the impedance value between the pair of electrode pads 5a and 5b is larger than the predetermined value, the AED control unit 10 may determine that the pair of electrode pads 5a and 5b are not attached to the surface of the body of the patient. When the result of the determination in the step S3 is No, the AED controller 10 stands by until the result of the determination in the step S3 becomes Yes.

When the result of the determination in the step S3 is Yes, the process proceeds to a step S4.

Next, the AED controller 10 determines whether the pair of electrode pads 5a and 5b are attached to the patient and a power-off operation has been performed on the power supply operating portion 4 or not (step S4). In the present example, the power-off operation is performed on the power supply operating portion 4 when the cover 2 is closed. Accordingly, the AED controller 10 determines whether the pair of electrode pads 5a and 5b are attached to the patient and the cover 2 has been closed or not. Moreover, the AED controller 10 determines whether the pair of electrode pads 5a and 5b are attached to the patient or not, based on the impedance value between the pair of electrode pads 5a and 5b, as described above.

When the result of the determination in the step S4 is Yes, the process proceeds to a step S13. On the other hand, when the result of the determination in the step S4 is No, the process proceeds to a step S5. Incidentally, in the present example, it is assumed that the pair of electrode pads 5a and 5b are attached to the patient. Therefore, in a state in which the electrode pads 5a and 5b are not attached to the patient and the power-off operation has been performed on the power supply operating portion 4, the power supply of the AED 1 is completely off. Therefore, processes in and after the step S5 are not executed. Furthermore, in a state in which the electrode pads 5a and 5b are not attached to the patient and the power-off operation has not been performed on the power supply operating portion 4 (the cover 2 has been opened), the AED controller 10 may visibly and/or audibly output guidance for prompting an operator to attach the electrode pads to the patient.

In the step S5, the AED controller 10 first receives ECG signals (an example of a physiological signal) of the patient through the pair of electrode pads 5a and 5b and the ECG processing circuit 18, and then analyzes an ECG of the patient based on the received ECG signals. The AED controller 10 may store the received ECG signals (ECG data) in the storage 13 or may transmit the ECG data to the management server on the communication network through the external communicator 12. Next, in a step S6, in a manner the same as or similar to the determination process in the step S4, the AED controller 10 determines whether the pair of electrode pads 5a and 5b are attached to the patient and the power-off operation has been performed on the power supply operating portion 4 or not. When the result of the determination in the step S6 is Yes, the AED controller 10 audibly and/or visually outputs guidance for prompting the operator to perform CPR (cardiopulmonary resuscitation) on the patient (step S11) after respective processes in steps S7 through S10 have been canceled.

On the other hand, when the result of the determination in the step S6 is No, the AED controller 10 determines whether a defibrillation process is necessary or not, based on the result of the ECG analysis (the step S7). Specifically, the AED controller 10 determines that the defibrillation process is necessary when the ECG of the patient shows arrhythmia such as ventricular fibrillation. On the other hand, the AED controller 10 determines that the defibrillation process is not necessary when the ECG of the patient shows no abnormality. When the result of the determination in the step S7 is No, the AED controller 10 audibly and/or visually outputs the guidance for prompting the operator to perform CPR on the patient (the step S11) after the processes in the steps S8 through S10 have been cancelled. When the result of the determination in the step S7 is Yes, the AED controller 10 visually and/or audibly outputs countdown notification prior to the start of the defibrillation process (the step S8). By viewing the countdown notification, the operator can clearly recognize that the defibrillation process will be automatically executed.

Next, in the step S9, the AED controller 10 determines whether the pair of electrode pads 5a and 5b are attached to the patient and the power-off operation has been performed on the power supply operating portion 4 or not. When the result of the determination in the step S9 is Yes, the AED controller 10 audibly and/or visually outputs the guidance for prompting the operator to perform CPR (cardiopulmonary resuscitation) on the patient (the step S11) after the defibrillation process in the step S10 has been canceled. When the result of the determination in the step S9 is No, the AED control unit 10 executes the defibrillation process of delivering an electric shock for defibrillation to the heart of the patient (the step S10). In this case, electrical energy that has been accumulated in the energy accumulator 17 is outputted from the electrode pads 5a and 5b through the high voltage generating circuit 16 and the pad connector 20.

Next, after the defibrillation process in the step S10 has been performed, the AED controller 10 determines whether a predetermined time (e.g. two minutes) has elapsed or not since a time point at which the guidance in the step S11 was outputted (step S12). When the predetermined time has not elapsed (No in the step S12), the AED controller 10 stands by until the predetermined time elapses while continuing the acquisition of the ECG signals of the patient. On the other hand, when the predetermined time has elapsed, the AED controller 10 executes the determination process in the step S3. Thus, as long as the power supply of the AED 1 is not off, the series of the processes shown in FIG. 4 are executed repeatedly.

Next, when the result of the determination in the step S3 is Yes, the AED controller 10 executes the determination process in the step S4. Here, when the result of the determination in the step S4 is Yes, the AED controller 10 first receives the ECG signals again through the pair of electrode pads 5a and 5b and the ECG processing circuit 18, and then analyzes the ECG of the patient again based on the received ECG signals (step S13). When, for example, the defibrillation process is canceled through the result of the determination in the step S6 or S9, the process in the step S13 is executed after the determination processes in the steps S3 and S4 have been executed again. In particular, in the case where the defibrillation process has been canceled, the pair of electrode pads 5a and 5b are attached to the patient, and the power-off operation has been performed on the power supply operating portion 4 (i.e. the cover 2 has been closed). Therefore, the determination in the step S4 results in Yes, so that the process in the step S13 is executed.

Next, in a manner the same as or similar to the determination process in the step S4, the AED controller 10 determines whether the pair of electrode pads 5a and 5b are attached to the patient, and the power-off operation has been performed on the power supply operating portion 4 or not (step S14). When the result of the determination in the step S14 is No, the process proceeds to the step S7. On the other hand, when the result of the determination in the step S14 is Yes, the process proceeds to a step S15. In the step S15, the AED controller 10 determines again whether the defibrillation process is necessary or not, based on the result of the ECG analysis. When the result of the determination in the step S15 is No, the AED control unit 10 audibly and/or visually outputs guidance (an example of second guidance) for prompting the operator to perform CPR on the patient (the step S11). When the result of the determination in the step S15 is Yes, the AED controller 10 audibly and/or visually outputs guidance (an example of first guidance) for prompting the operator to perform the defibrillation process on the patient (step S16). Here, a message such as "An electric shock is necessary. To deliver the electric shock to the patient, please open the cover 2." may be outputted audibly and/or visually as an example of the guidance for prompting the operator to perform the defibrillation process. Next, the AED controller 10 determines whether the pair of electrode pads 5a and 5b are attached to the patient and the power-off operation has been performed on the power supply operating portion 4 or not (step S17). When the result of the determination in the step S17 is No, the process proceeds to the step S8. On the other hand, when the result of the determination in the step S17 is Yes, the process proceeds to the step S11. Thereafter, the processes in and after the step S3 are executed repeatedly through the determination process in the step S12.

According to the present embodiment, it is determined whether the pair of electrode pads 5a and 5b are attached to the patient and the power-off operation has been performed on the power supply operating portion 4 or not (i.e. the cover 2 has been closed or not). According to the result of the determination, the defibrillation process of delivering an electric shock to the patient is canceled while the on state of the power supply of the AED 1 is maintained. Thus, in a situation where the patient regains consciousness before execution of the defibrillation process, the defibrillation process can be canceled while the on state of the power supply of the AED 1 is maintained. In this respect, according to the background-art fully automatic AED, the power supply of the AED has to be completely turned off in order to cancel a defibrillation process. Therefore, to analyze an ECG of the patient again, there is a waiting time until the AED moves to an ECG analysis process after the AED is reactivated. On the other hand, in the present embodiment, only the defibrillation process of the AED 1 can be canceled while the on state of the power supply of the AED 1 is maintained. In other words, in comparison with the background-art AED that has to be completely powered off, the AED 1 according to the present embodiment can, for example, omit the initialization processes (the step S1) that are executed when the AED 1 is activated. Furthermore, even after the defibrillation process has been canceled, the ECG analysis of the patient is continued, and the determination as to whether the defibrillation process is necessary or not is continued. In other words, even after the defibrillation process has been canceled, the AED control unit 10 continuously receives the ECG signals (ECG data) of the patient. Due to the continuous acquisition of the ECG signals (ECG data), the condition of the patient can be referred to later even after the defibrillation process has been canceled. In this manner, usability of the AED 1 can be spectacularly improved in a scene where the operator wants to cancel the defibrillation process.

In addition, in the present embodiment, the power-off operation is performed on the power supply operating portion 4 when the cover 2 is closed. Thus, in the state in which the electrode pads 5a and 5b are attached to the patient, the operator can cancel the defibrillation process by closing the cover 2. Accordingly, by a relatively simple operation, the defibrillation process can be canceled while the on state of the power supply is maintained.

In addition, the guidance for prompting the operator to perform the defibrillation process (the step S16) and the guidance for prompting the operator to perform CPR on the patient (the step S11) are outputted audibly and/or visually. Thus, the operator can give appropriate treatment to the patient through the guidances. In particular, the guidance for prompting the operator to perform the defibrillation process is outputted via the processes in the step S12, the steps S3 and S4, and the steps S13 through S15 after the defibrillation process in the step S10 has been canceled. Accordingly, the operator can clearly recognize the necessity of performing the defibrillation process on the patient through the guidance.

The embodiment of the present disclosure has been described above. However, the technical scope of the present disclosure should not be limitedly interpreted by the description of the present embodiment. The present embodiment is merely exemplified, and it is understood by those skilled in the art that various modifications can be made on the embodiment within the scope of the invention described in CLAIMS. The technical scope of the present disclosure should be defined based on the scope of the invention described in the CLAIMS and its equivalent scopes.

For example, in the present embodiment, the defibrillation process is canceled according to the result of the determination as to whether the electrode pads 5a and 5b are attached to the patient and the power-off operation has been performed on the power supply operating portion 4 or not. However, the present embodiment is not limited thereto. In this respect, the AED controller 10 may cancel the defibrillation process according to the result of the determination as to whether the electrode pads are attached to the patient and a predetermined operation (such as an operation on a predetermined button provided in the AED 1) has been performed on the AED 1 or not. In addition, in the present embodiment, the power-on operation or the power-off operation is performed on the power supply operating portion 4 in response to the opening or closing of the cover 2. However, the power-on operation or the power-off operation does not have to be associated with the opening or closing of the cover 2.

The sequence of the series of processes shown in FIG. 4 is merely exemplified, and the sequence of the processes may be changed appropriately.

The invention claimed is:

1. An automated external defibrillator configured to automatically execute a defibrillation process of delivering an electric shock for defibrillation to a heart of a subject, the automated external defibrillator comprising:
   a power supply operating portion for turning on or off a power supply of the automated external defibrillator;
   a processor; and
   a memory that stores a computer-readable instruction that when executed by the processor, causes the automated external defibrillator to perform operations comprising:
   receiving a physiological signal of the subject through an electrode pad;
   determining whether the defibrillation process is necessary based on the physiological signal;
   determining whether the electrode pad is attached to the subject;
   determining whether an operation for turning off the power supply has been performed on the power supply operating portion, and
   based on a determination that the defibrillation process is necessary, a determination that the electrode pad is attached to the subject, and a determination that the operation for turning off the power supply has been performed on the power supply operating portion, cancelling the defibrillation process while maintaining an on-state of the power supply of the automated external defibrillator.

2. The automated external defibrillator according to claim 1, wherein based on the determination that the defibrillation process is necessary, the determination that the electrode pad is attached to the subject, and a determination that the operation for turning off the power supply has not been performed on the power supply operating portion,
   the automated external defibrillator does not cancel the defibrillation process.

3. The automated external defibrillator according to claim 1, wherein
   after the automated external defibrillator has canceled the defibrillation process while maintaining the on-state of the power supply, the automated external defibrillator continues to receive the physiological signal of the subject, and continues to determine whether the defibrillation process is necessary or not based on the physiological signal.

4. The automated external defibrillator according to claim 1, further comprising:
   a housing; and
   a cover that is connected to the housing, wherein
   the cover is opened when an operation for turning on the power supply is performed on the power supply operating portion; and
   the operation for turning off the power supply is performed on the power supply operating portion when the cover is closed.

5. The automated external defibrillator according to claim 1, wherein
   the electrode pad has a pair of electrode pads, and
   the automated external defibrillator determines whether the pair of electrode pads are attached to the subject or not, based on an impedance value between the pair of electrode pads.

6. The automated external defibrillator according to claim 1, wherein
   the automated external defibrillator is configured to:
   turn on the power supply when an operation for turning on the power supply has been performed on the power supply operating portion; and
   turn off the power supply when the electrode pad is not attached to the subject and the operation for turning off the power supply has been performed on the power supply operating portion.

7. The automated external defibrillator according to claim 1, further comprising:
   an output portion that audibly or visually presents first guidance for prompting an operator to perform the defibrillation process and/or second guidance for prompting the operator to perform cardiopulmonary resuscitation on the subject.

8. The automated external defibrillator according to claim 7, wherein
   the automated external defibrillator audibly or visually presents the second guidance through the output portion after the defibrillation process has been executed or canceled.

9. The automated external defibrillator according to claim 7, wherein
   after the automated external defibrillator has canceled the defibrillation process while maintaining the on state of the power supply,
   the automated external defibrillator determines again whether the defibrillation process is necessary or not based on the physiological signal of the subject, and audibly or visually presents the first guidance through the output portion when the defibrillation process is necessary.

\*    \*    \*    \*    \*